United States Patent
Sildve et al.

(10) Patent No.: US 6,863,440 B2
(45) Date of Patent: Mar. 8, 2005

(54) HEAD POSITIONING APPARATUS AND METHOD FOR CEPHALOMETRIC IMAGING

(75) Inventors: Peter Sildve, Glen Ellyn, IL (US); Randall Wick, Roselle, IL (US)

(73) Assignee: B.F. Wehmer Co., Inc., Addison, IL (US)

( * ) Notice: Subject to any disclaimer, the term of this patent is extended or adjusted under 35 U.S.C. 154(b) by 332 days.

(21) Appl. No.: 09/791,189

(22) Filed: Feb. 22, 2001

(65) Prior Publication Data

US 2002/0114427 A1 Aug. 22, 2002

(51) Int. Cl.$^7$ ................................................ H05G 2/00
(52) U.S. Cl. ..................... 378/208; 378/195; 378/177
(58) Field of Search ......................... 378/208, 177, 378/179, 195, 170, 168, 39, 38; 128/303; 250/491

(56) References Cited

U.S. PATENT DOCUMENTS

| | | | |
|---|---|---|---|
| 2,264,410 A | * | 12/1941 | Schier ........................ 378/41 |
| 3,536,913 A | | 10/1970 | Huchel et al. |
| 3,790,803 A | | 2/1974 | Phillips |
| 3,875,412 A | * | 4/1975 | Hozumi ..................... 378/208 |
| 3,906,227 A | | 9/1975 | Ensslin et al. |
| 4,088,893 A | | 5/1978 | Schroeder |
| 4,125,774 A | | 11/1978 | Ciavattoni et al. |
| 4,144,460 A | | 3/1979 | Norman |
| 4,256,112 A | * | 3/1981 | Kopf et al. ................. 606/130 |
| 4,400,826 A | | 8/1983 | Preti et al. |
| 4,566,444 A | | 1/1986 | Spolyar |
| 4,579,117 A | | 4/1986 | Spolyar |
| 4,683,582 A | | 7/1987 | Spolyar |
| 4,759,361 A | | 7/1988 | Gallop et al. |
| 4,760,591 A | | 7/1988 | Gallop et al. |
| 4,907,251 A | | 3/1990 | Mork et al. |
| 4,979,519 A | | 12/1990 | Chavarria et al. |
| 5,058,147 A | | 10/1991 | Nishikawa et al. |
| 5,160,262 A | | 11/1992 | Alpern et al. |
| 5,263,494 A | | 11/1993 | Margelos et al. |
| 5,320,528 A | | 6/1994 | Alpern et al. |
| 5,325,415 A | | 6/1994 | Coffman |
| 5,513,240 A | | 4/1996 | Hausmann et al. |
| 5,612,985 A | * | 3/1997 | Toki et al. ..................... 378/4 |
| 5,629,972 A | | 5/1997 | Hausmann et al. |
| 5,642,392 A | | 6/1997 | Nakano et al. |
| 5,692,027 A | | 11/1997 | Yoshimura et al. |

* cited by examiner

*Primary Examiner*—Edward J. Glick
*Assistant Examiner*—Hoon Song
(74) *Attorney, Agent, or Firm*—Wildman, Harrold, Allen & Dixon, LLP; Thomas J. Ring (57) ABSTRACT

A apparatus is described for positioning the head of a patient for taking various x-ray images of the head. The head-positioning apparatus contemplates an arm member rotatably mounted to a pivot member for rotating the arm about an axis of rotation and at least one ear locating member coupled to the arm member in which the ear locating member rotates with the arm member and in alignment with the axis of rotation. The apparatus also contemplates an x-ray emitting source and an indicator coupled to the x-ray emitting source to provide the indicator and x-ray emitting source to rotate in conjunction and same direction with each other, in which the indicator locates a plane alignable with an ear of the patient.

82 Claims, 2 Drawing Sheets

HEAD POSITIONING APPARATUS AND METHOD FOR CEPHALOMETRIC IMAGING

FIELD OF THE INVENTION

The present invention relates to an apparatus used to position a patient's head for x-ray imaging, and to methods for using the apparatus to obtain various x-ray images of the patient's head.

DETAILED DESCRIPTION

Figure 1:
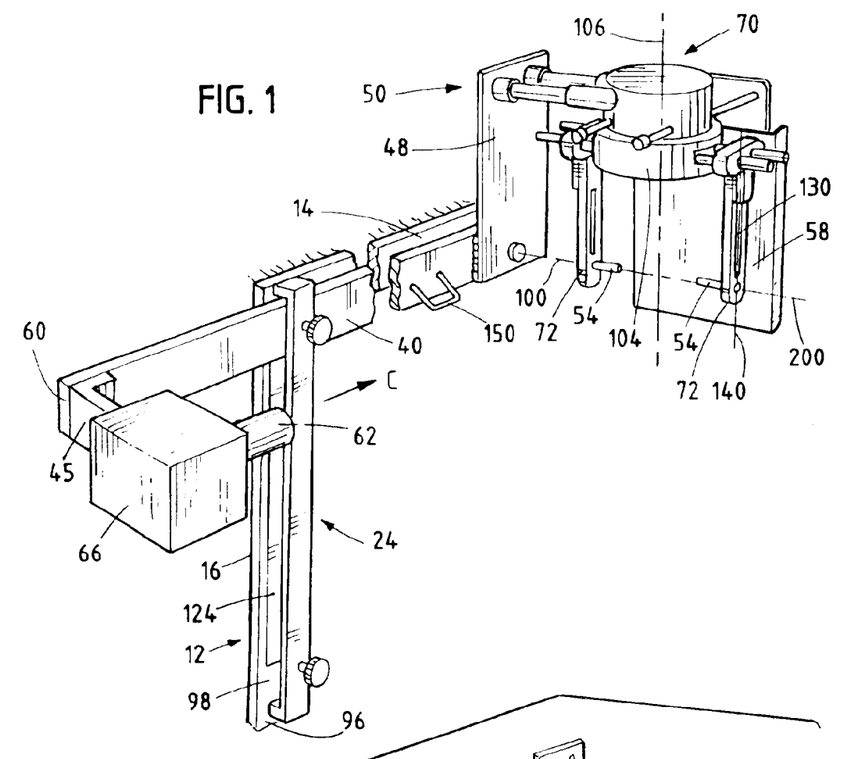
FIG. 1 is a perspective view of one embodiment of the head-positioning apparatus of the present invention.
Figure 2:
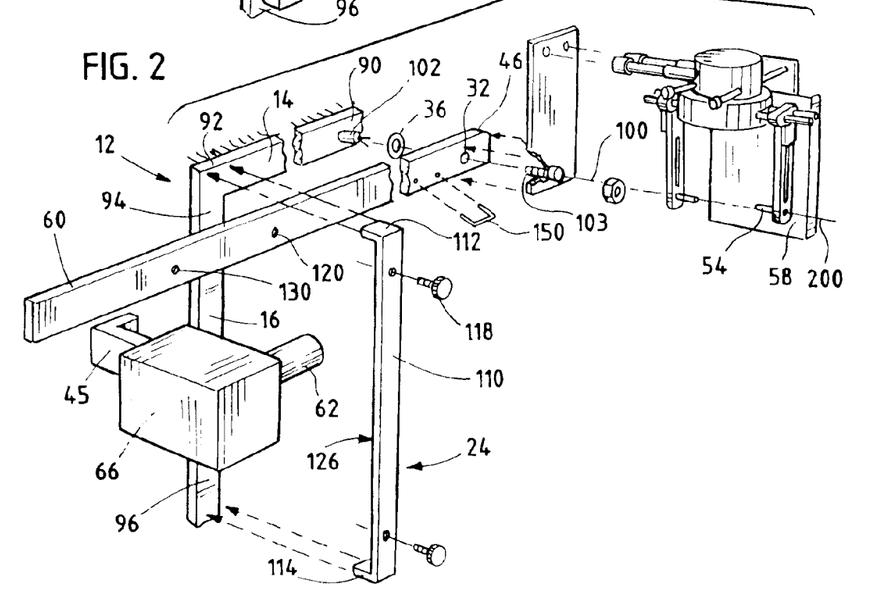
FIG. 2 is an exploded perspective view of the apparatus of FIG. 1.

Referring to FIGS. 1 and 2, a rotatable arm member 40 is provided to which various components of an x-ray imaging system are attached. Arm member 40 has an end 60 and an opposing end 46. An imaging system component such as an x-ray emitting source 66 is mounted to arm member 40 proximate end 60 utilizing a projecting portion 45. This construction permits the movement of x-ray emitting source 66.

Arm member 40 is of sufficient length to provide a desired spacing of sixty inches between x-ray emitting source 66 mounted to end 46 and a midsaggital plane of a patient (an imaginary vertical plane generally aligned with the face of a patient) when the head of the patient is positioned by an ear locating member 54 coupled to arm member 40 as described in greater detail below. To provide the desired spacing in the presently described embodiment, the length of arm member 40 is determined so as to enable a spacing of between 50 inches and 70 inches between an x-ray emitting source mounted on projecting portion 45 and an axis of rotation 100 of arm member 40.

A gripping member 150 may project from arm member 40 intermediate arm member ends 60 and 46 for grasping by the patient to help stabilize his position during the radiography session.

A hole 32 is provided in arm member 40 intermediate end 60 and opposing end 46 for receiving a bearing (not shown) which accepts a pivot member 102 on which arm member 40 is rotationally mounted through bolt 103.

In various embodiments, arm member 40 may be rotatably mounted to a wall, floor, ceiling or other surface. Alternatively, arm member 40 may be rotatably mounted on a support member. The support member with arm member 40 thereon may then be affixed to a wall, floor, ceiling or other surface, or the support member may form a transportable base permitting transportation of arm member 40 to different locations.

FIG. 1 shows one particular embodiment in which arm member 40 is rotatably mounted to a support member 12 which is mounted to a wall. Support member 12 is shown in greater detail in FIG. 2. In this embodiment support member 12 has an "L" shape, although support member 12 may have any one of numerous alternatives shapes. Support member 12 has a first portion 14 which extends generally parallel to a floor and includes a first end 90 and a second end 92. Support member 12 also has a second portion 16 projecting from support member first portion 14 in a direction generally perpendicular to support member first portion 14. Second portion 16 of support member 12 has a first end 94 intersecting first portion second end 92, and a second end 96. Support member first portion 14 and second portion 16 should be of sufficient length to provide support and guidance for arm member 40 through its entire range of rotation. In this embodiment, support member first portion 14 is approximately 42 inches long and support member second portion 16 is approximately 30 inches long.

A pivot member 102 is provided for rotatably connecting arm member 40 to a wall, support member or other surface for rotation about an axis of rotation 100. Referring to FIG. 2, in the presently described embodiment pivot member 102 comprises a pin or other cylindrical member. A washer 36 is slid onto pivot pin 102 so as to be interposed between arm member 40 and support member 12 when arm member 40 is mounted on pivot pin 102. Arm member 40 is secured to support member 12 by passing a threaded end of pivot pin 102 through arm member hole 32 and applying a nut 38 thereto. Numerous other commonly known ways of rotatably connecting two components together are contemplated herein.

Rotation of arm member 40 on pivot member 102 may be manually actuated or motorized. If rotation of arm member 40 is to be manually actuated, arm member 40 may be coupled to a counterweight system (not shown) for counterbalancing the weight of any imaging system components mounted on arm member 40 during arm member rotation. Commonly known ways of assisting movement of arm member 40 are contemplated herein.

Referring to FIG. 1, an imaging system is mounted on arm member 40. Many types of imaging systems are commonly known and are contemplated herein. The presently described embodiment includes a collimator 62 and an x-ray emitting source 66 mounted to projecting member 45, and a x-ray film plate holder 58 mounted proximate opposing end 46 of arm member 40. Holder 58 is spaced apart from axis of rotation 100 so as to receive x-rays emitted from x-ray emitting source 66 which pass through collimator 62 and travel in a direction indicated by arrow "C". As is known in the art, collimator 62 acts to focus x-rays emitted from x-ray emitting source 66. X-ray emitting source 66 is mounted on projecting member 45 such that the center of an x-ray beam emanating from the source is aimed at rotational axis 100 and at a line 200 extending through longitudinal ear locating members 54. As well as being mounted directly onto projecting member 45, x-ray emitting source 66 is also contemplated to be positioned separately from arm member 40. Whether x-ray emitting source 66 is positioned separately from arm member 40 or mounted thereon, the x-ray emitting source is positioned so as to enable emission of x-rays toward arm member rotational axis 100.

As seen in FIG. 1, at least one ear locating member 54 is coupled to arm member 40 for enabling positioning of the head of a patient in a predetermined orientation. Ear locating member 54 rotates with arm member 40 and is capable of rotating with arm member 40 in alignment with axis of rotation 100. Ear locating member 54 has a generally longitudinal configuration suitable for insertion into an ear of a patient such that translational movement of the head of a patient is prevented, thereby locating and maintaining the ear and head in a desired position in space, while allowing rotational movement of the head relative to ear locating member 54 about axis 100.

In the presently described embodiment, a pair of ear locating members 54 is incorporated into a bracket apparatus 50 affixed to arm member 40 and x-ray film plate holder 58. In this embodiment, bracket apparatus 50 comprises a mounting plate 48 affixed to arm member 40 and a head fixator 70 affixed to mounting plate 48. Head fixator 70, for example, is embodied in the head fixator disclosed in McArdle et al., U.S. Pat. No. 4,974,243, the description of which is incorporated herein.

As seen in FIG. 1, head fixator 70 includes a pair of ear locating member brackets 72 each of which has a round-tipped ear locating member 54 secured thereto. As in other head fixator devices, ear locating members 54 are used to properly position and immobilize the head of the patient. Brackets 72 are supported on sliding blocks (for adjustable separation) to accommodate heads of various sizes and to engage the ears of the patient. These blocks are positioned for linear movement with respect to a rotating cam plate, Camrol bearing and guide plate (not shown) to provide an equidistant telescoping movement along axis 200 extending through longitudinal ear locating members 54. The sliding blocks are slidably received within the slide members in a closely fitting connection controlled by adjustable gibs (not shown) which admits very little lateral movement and maintains ear locating member brackets 72 and ear locating members 54 in a predetermined position. Brackets 72 are connected to a rotator assembly 104 which enables rotation of the brackets about an axis 106 transverse to arm member axis of rotation 100, as indicated in FIG. 1. In the presently described embodiment, axis 106 is perpendicular to arm member axis of rotation 100. Also in the presently described embodiment, axis 106 intersects arm member axis of rotation 100. Rotator assembly 104 and brackets 72 connected thereto are capable of 360° rotation about axis 106 and have index stops lockable at every 45° in their circular range of rotation about this axis.

Referring to FIG. 1, the head positioning system of the present invention provides an indicator for use in determining when a predetermined diagnostic plane passing through the head of a patient is properly oriented with respect to x-ray emitting source 66 for obtaining a desired x-ray view of the head. For purposes to be described later, the indicator of the presently described embodiment comprises an elongated slot 130 incorporated into at least one of ear locating member brackets 72. Indicator slot 130 extends along a longitudinal axis 140 running generally parallel to axis of rotation 106 and locates a plane which is transverse to direction "C" of emission of x-rays from x-ray emitting source 66. Indicator slot 130 is also positionable to intersect axis of rotation 100 with ear locating members 54 positionally aligned with axis of rotation 100. As indicator slot 130 is incorporated into at least one of brackets 72, and as brackets 72 are affixed to arm member 40 via head fixator 70, indicator slot 130 will rotate in conjunction with, and in the same direction as, arm member 40 and x-ray emitting source 66 about arm member axis of rotation 100.

Indicator slot 130 is provided such that the head of the patient will be visible through slot 130 when ear locating member 54 attached to bracket 72 is inserted into the ear canal of the patient. Bracket 72, or a portion of the bracket incorporating indicator slot 130, may be formed such that slot 130 is an opening through bracket 72. Bracket 72 may be formed from a transparent or translucent material to provide a clearer visual indication of the orientation of the patient's head. The indicator of the present invention is contemplated to take on numerous constructions which will identify a plane. In the presently described embodiment, the plane identified is perpendicular to the direction of emission of the x-rays. The plane intersects arm member axis of rotation 100 and is alignable with ear locator members 54. Typically, a plane of this nature can be located by use of two points that the plane will intersect or by identifying a line included in the plane. Thus, the indicator can include a point or area location which are contained in the plane. For example, an opening positioned in bracket 72 positioned above ear locator member 54 can locate the plane. An elongated member aligned to intersect arm member axis of rotation 100 and extending upwardly can also accomplish this task. Alternatively, a single line (or one or more parallel lines) may be provided on a bracket which is formed from a transparent or translucent material. The line (or lines) would extend along a longitudinal axis running parallel to axis of rotation 106 and define a plane which is transverse or, as in the presently described embodiment, perpendicular to the direction of emission of the x-rays. Various target markings or structures, lines, slots and other corresponding known ways of locating a plane are also contemplated herein.

As shown in FIG. 1, head fixator 70 is secured to a mounting plate 48 which is attached to arm member 40. When attached to mounting plate 48 head fixator 70 is secured with respect to arm member 40 such that head fixator 70 rotates in conjunction with arm member 40. Head fixator 70 is also rotatable about axis 106 such that line 200 extending through ear locator members 54 may be coaxially aligned with arm member axis of rotation 100.

Referring to FIG. 1, a first friction reduction element 124 may be positioned on an outer surface 98 of support member second portion 16 so as to be interposed between support member second portion 16 and arm member 40 during movement of arm member 40 with respect to support member 12. This construction is to facilitate smooth relative motion of arm member 40 with respect to second portion 16 of support member 12 and reduce wear on these components. In the presently described embodiment, first friction reduction element 124 comprises a strip formed from a material (a plastic, for example) that will, when in contact with arm member 40 during arm member movement, produce a coefficient of kinetic friction which is less than the friction coefficient produced by moving contact between arm member 40 and the outer surface of second portion 16 of support member 40.

Referring to FIG. 2, an alignment member may be attached to support member 12 to aid in restricting the rotational motion of arm member 40 to within a predetermined plane. In the presently described embodiment, the alignment member comprises a generally "U"-shaped bracket 24 secured to second portion 16 of support member 12 proximate second portion first end 94 and second end 96. Bracket 24 comprises an elongated main body having opposing ends and spacing projections 112, 114 extending from the opposing ends, for spacing bracket main body 110 of the bracket from support member 12 and enabling attachment of bracket 24 to support member 12. Bracket 24 also has an inner surface 126 which resides opposite outer surface 98 of support member second portion 16. If arm member 40 is mounted directly to a wall, bracket 24 may also be secured directly to the wall to perform the alignment function. In addition, many commonly known alternative types of alignment members are contemplated and can be used.

A second friction reduction element (not shown) may be positioned on bracket inner surface 126 so as to be interposed between bracket 24 and arm member 40 during movement of arm member 40 with respect to support member 12. In a manner similar to first friction reduction element 124, the second friction reduction element provides smooth relative motion of arm member 40 with respect to bracket 24 and reduces wear on these components.

In an embodiment of the present invention in which arm member 40 is manually rotated, an arm member locking device may be incorporated for securing arm member 40 in a first predetermined angular position. As seen in FIG. 2, the locking device comprises a spring loaded plunger 118 provided for securing arm member end 60 such that arm member 40 is in a horizontal position. Spring loaded plunger 118 is attached to alignment member 24 proximate first end 94 of second portion 16 of support member 12. A complimentary hole 120 is provided in arm member 40 for receiving an end of spring loaded plunger 118 therein when arm member 40 is in the horizontal position. In addition, other configurations and types of locking devices incorporating features such as threaded plungers or clamps are contemplated, as well as other commonly known structures used to accomplish this function.

A second locking device comprising a second spring loaded plunger 128 may be located proximate second end 96 of frame second portion 16 for securing arm member 40 second end such that arm member 40 is in a second predetermined angular position (in this embodiment, approximately 25 degrees below the horizontal) with respect to frame 12. Second spring loaded plunger 128 is positioned in alignment member 24 proximate second end 96 of frame second portion 16. A complimentary hole 130 is located in arm member 40 proximate arm member second end 60 for insertion of second spring loaded plunger 128 therein when arm member 40 has been rotated to the second predetermined angular position.

Alternatively, a hard stop or other equivalent structure may be provided for maintaining arm member 40 in the second predetermined angular position. The hard stop may be provided by, for example, a spacing projection 114 extending from an end of alignment member 24.

In other alternative embodiments, the head positioning apparatus described above may be mounted onto a support member mounting structure comprising a frame, one or more brackets or a similar structure configured to allow repositioning of the head positioning apparatus with respect to the wall, floor or ceiling. The support member mounting structure may, for example, comprise a pair of parallel rails affixed to a wall, portions of the support member being configured to slide along these rails. The rails may alternatively be affixed to a floor or ceiling. Also, a motorized positioning mechanism may be included to enable selective positioning of the head positioning apparatus with respect to the wall, floor or ceiling. Alternatively, a manual positioning device may be used to locate the head positioning apparatus along the rails. A securement device may be used to secure the head positioning apparatus in a desired position along the rails. The securement device may comprise a spring loaded plunger or other equivalent device.

Methods for using the above-described head-positioning apparatus to obtain various x-ray images of the head of a patient will now be discussed.

Figures 3, 4, 5:
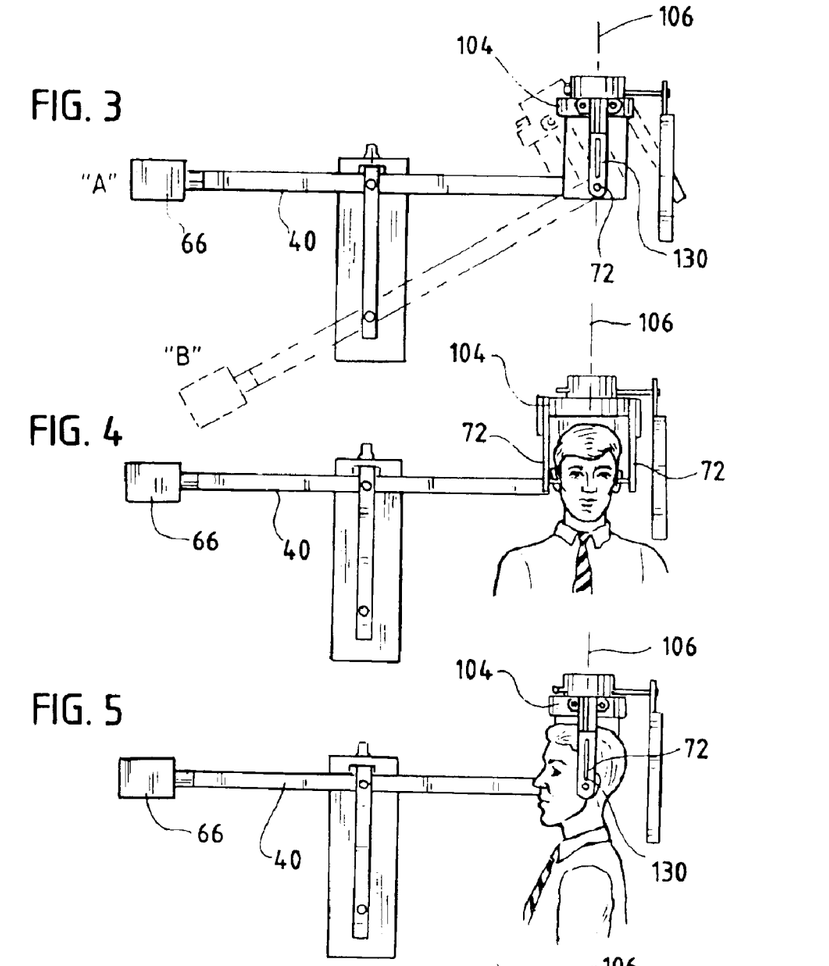
FIG. 3 is a side view of the head-positioning apparatus of FIG. 1 showing a range of rotation of an arm member and components attached thereto.
FIG. 4 is a side view head-positioning apparatus of FIG. 1 showing an apparatus for positioning the head of a patient for obtaining a lateral x-ray view of the patient's head.
FIG. 5 is a side view head-positioning apparatus of FIG. 1 showing an apparatus for positioning the head of a patient for obtaining an anterior (frontal) x-ray view of the patient's head.

FIG. 3 is a side view of the head-positioning apparatus of FIG. 1 showing a range of rotation of arm member 40 about arm member axis of rotation 100 between a first predetermined angular position "A" and a second predetermined angular position "B". The range of arm rotation needed for a particular embodiment of the apparatus will be affected by the height of arm member axis of rotation 100 above the floor, as well as by other factors. As discussed above, the location of the head-positioning apparatus with respect to the floor may be adjusted in certain embodiments. Thus, the present invention contemplates a range of arm rotation from the horizontal to between 20 and 50 degrees below the horizontal. In the presently described embodiment, first angular position "A" of arm member 40 is horizontal and second angular position "B" of arm member 40 is approximately 25 degrees below the horizontal. The head-positioning apparatus is positioned in the horizontal orientation for obtaining a lateral x-ray view and an anterior x-ray view of the head of a patient. The head-positioning apparatus is rotated to approximately 25 degrees below the horizontal for obtaining a submental vertex x-ray view of the head of the patient.

FIG. 4 is a side view of the head-positioning apparatus for positioning the head of a patient for obtaining a lateral x-ray view of the head of the patient. To position the head of the patient for obtaining a lateral x-ray view, arm member 40 is locked in the first (horizontal) angular position. Rotator assembly 104 is rotated about axis 106 until line 200 extending through ear locating members 54 is perpendicular to arm member rotational axis 100. Rotator assembly 104 is then locked in position. With the patient facing in the general direction opposite arm member 40, the head of the patient is then secured in the head-positioning apparatus by inserting ear locating members 54 into respective ear canals of the patient. An x-ray view of the head of the patient is then taken in this position.

FIG. 5 is a side view of the head-positioning apparatus for positioning the head of a patient for obtaining an anterior (frontal) x-ray view of the head of the patient. To position the head of a patient for obtaining an anterior x-ray view, rotator assembly 104 is rotated about axis 106 until line 200 extending through ear locating members 54 is coaxial with arm member rotational axis 100. Rotator assembly 104 is then locked in position. With the patient facing in the general direction of x-ray emitting source 66, the head of the patient is secured in the head-positioning apparatus by inserting ear locating members 54 into respective ear canals of the patient. An x-ray view of the head of the patient is then taken in this position.

Figure 6:
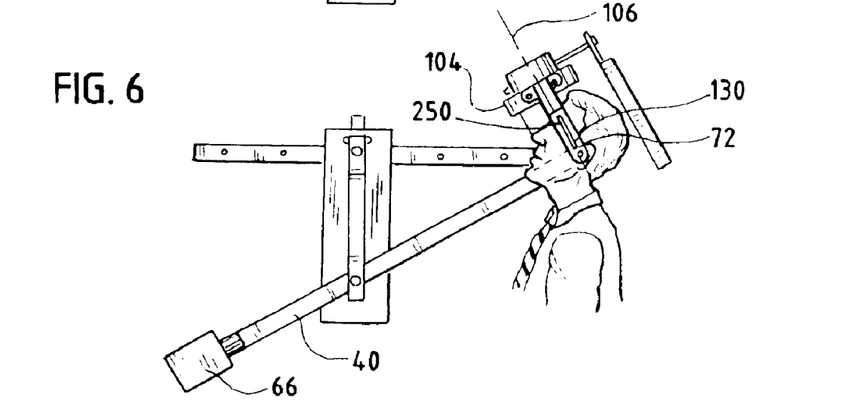
FIG. 6 is a side view head-positioning apparatus of FIG. 1 showing an apparatus for positioning the head of a patient for obtaining a submental vertex x-ray view of the patient's head.

FIG. 6 is a side view of the head-positioning apparatus for positioning the head of a patient for obtaining a submental vertex x-ray view of the head of the patient. As is known in the art, a submental vertex view is a view taken from beneath the chin of a patient and through the top of the head.

For purposes of obtaining a submental vertex view, indicator slot 130 is oriented with respect to x-ray emitting source 66 such that x-rays emanating therefrom impinge a plane located by indicator slot longitudinal axis 140, at right angles to the plane. As indicator slot 130 and x-ray emitting source 66 are mounted on arm member 40 and rotate in conjunction with each other, the desired relationship between these elements is maintained for every angular position of arm member 40.

The plane located by indicator slot longitudinal axis 140 is used to indicate proper orientation of a specific diagnostic plane of the patient with respect to x-ray emitting source 66. In the presently described embodiment, the specific diagnostic plane of interest is known as the Frankfort plane. As is known in the art, the Frankfort plane is defined by a line joining an ear canal opening of the patient and the lower eye socket adjacent the ear canal. More particularly, the patient is determined to be properly oriented with respect to x-ray emitting source 66 when the Frankfort plane of the patient is coplanar with a plane located by indicator slot longitudinal axis 140.

To help identify when the Frankfort plane of the patient is coplanar with a plane located by indicator slot longitudinal axis 140, an indicator mark 250 is applied to the face of the patient at the lower portion of the eye socket adjacent an ear to be positioned by one of ear positioning members 54. Indicator mark 250 serves as a visual indication of one point used to identify the Frankfort plane of the patient, the other identifying point being the ear canal of the patient. The indicator mark may comprise, for example, an adhesive patch or a mark made using removable ink.

To position the head of a patient for obtaining a submental vertex x-ray view, arm member 40 is rotated to the second angular position (approximately 25 degrees below the horizontal) and locked in position. Rotator assembly 104 is rotated about axis 106 until a line extending through ear positioning members 54 is coaxial with arm member rotational axis 100. Rotator assembly 104 is then locked in position. With the patient facing in the general direction of x-ray emitting source 66, the head of the patient is secured in the head-positioning apparatus by inserting ear locating members 54 into respective ear canals of the patient. The head of the patient is then rotated about ear positioning members 54 until indicator mark 250 applied to the face of the patient adjacent ear locating member bracket 72 is visible in indicator slot 130 and intersects a plane located by indicator longitudinal axis 140. Indicator longitudinal axis 140 intersects line 200 extending through ear positioning members 54. Ear positioning members 54 are inserted into the ear canals of the patient. Therefore, when the head is positioned such that both indicator mark 250 and the ear canal adjacent indicator mark 250 lie on a plane located by indicator longitudinal axis 140, the Frankfort plane of the patient is determined to be coplanar with the plane located by indicator longitudinal axis 140; thus, the desired orientation of the head has been achieved. An x-ray view of the head of the patient is then taken in this position.

If it is desired to take anterior and submental vertex views in sequence, arm member 40 may be rotated from first angular orientation "A" to second angular orientation "B" (or vice versa) while the patient remains secured in the head-positioning apparatus, thereby minimizing movement of the patient between successive views.

As previously stated, rotator assembly 104 and brackets 72 connected thereto are capable of 360° rotation about axis 106 and have index stops lockable at every 45° in their circular range of rotation about this axis. Thus, in addition too the above-mentioned views, the head-positioning apparatus of the present invention may be used to obtain oblique views of the head of a patient. To position the head of a patient for obtaining a oblique x-ray view, arm member 40 is locked in the horizontal position. Rotator assembly 104 is rotated about axis 106 until a line extending through the center of an x-ray beam emanating from source 66 intersects line 200 extending through the ear locating members at an acute angle. In the presently described embodiment, as rotator assembly 104 is lockable every 45°, the acute angle formed by the intersection of the above-described lines would be 45°. An x-ray view of the head of the patient is then taken in this position. Oblique views at other angles would be possible depending the rotational positions about axis 106 at which rotator assembly 104 could be secured.

It should be understood that the preceding is merely a detailed description of one embodiment of this invention and that numerous changes to the disclosed embodiment can be made in accordance with the disclosure herein without departing from the spirit or scope of the invention. The preceding description, therefore, is not meant to limit the scope of the invention. Rather, the scope of the invention is to be determined only by the appended claims and their equivalents.

What is claimed is:

1. An apparatus utilized to position a head of a patient for taking an x-ray image of the head, comprising:
   an arm member rotatably mounted to a pivot member for rotating the arm about an axis of rotation;
   an x-ray emitting source mounted to the arm member; and
   at least one ear locating member coupled to the arm member in which the ear locating member rotates with the arm member and is positioned in the axis of rotation.

2. The apparatus of claim 1 wherein the pivot member is associated with at least one of the floor and wall.

3. The apparatus of claim 2 wherein the pivot member is mounted to a support member for mounting to at least one of a floor a wall.

4. The apparatus of claim 1 wherein the arm member is elongated.

5. The apparatus of claim 1 wherein the x-ray emitting source is spaced apart from the axis of rotation.

6. The apparatus of claim 5 wherein the x-ray emitting source is positioned for emitting x-rays toward the axis of rotation.

7. The apparatus of claim 5 wherein the x-ray emitting source is positioned closer to an end of the arm member than to the axis of rotation.

8. The apparatus of claim 7 wherein the axis of rotation is positioned closer to an opposing end of the arm member than to the x-ray emitting source.

9. The apparatus of claim 5 wherein the x-ray emitting source is positioned in a range between 50 inches and 70 inches from the axis of rotation.

10. The apparatus of claim 5 including an x-ray film plate holder fixedly secured to the arm member and spaced apart from the axis of rotation on an opposite side of the axis of rotation from the x-ray emitting source.

11. The apparatus of claim 10 including a bracket apparatus fixedly secured to the x-ray film holder and fixedly secured to the arm member.

12. The apparatus of claim 10 wherein the x-ray film plate holder is aligned with the axis of rotation and the x-ray emitting source such that the x-ray film plate holder receives x-rays from the x-ray emitting source.

13. The apparatus of claim 1 wherein the ear locating member is coupled to the arm member with an ear locator bracket member carrying the ear locator member and with the ear locator bracket member connected to a bracket apparatus which is fixedly mounted to the arm member.

14. The apparatus of claim 13 wherein the ear locator bracket member is rotatably mounted to the bracket apparatus permitting the at least one ear locator member to rotate about another axis of rotation transverse to the axis of rotation.

15. The apparatus of claim 14 wherein the other axis of rotation is perpendicular to the axis of rotation.

16. The apparatus of claim 15 wherein the axis of rotation and the other axis of rotation intersect one another.

17. An apparatus utilized for taking an x-ray of a head of a patient, comprising:
an x-ray emitting source; and
an indicator coupled to the x-ray emitting source to provide the indicator and x-ray emitting source to rotate in conjunction and same direction with each other, in which the indicator locates a plane alignable with an ear of the patient; wherein
the indicator to locate the plane is coupled to the x-ray emitting source such that the indicator of the plane and the x-ray emitting source are rotatable about the same axis of rotation.

18. The apparatus of claim 17 wherein the indicator is visual.

19. The apparatus of claim 17 wherein the plane is positioned transverse to a direction of emission of x-rays from the x-ray emitting source.

20. The apparatus of claim 17 wherein the plane is maintained in the transverse position.

21. The apparatus of claim 19 wherein the plane is perpendicular to the direction of the emission of x-rays.

22. The apparatus of claim 17 wherein an ear locator number is coupled with the x-ray emitting source, aligned with the axis of rotation and alignable with the ear of the patient.

23. The apparatus of claim 17 wherein the x-ray emitting source is spaced apart from the axis of rotation.

24. The apparatus of claim 17 wherein the indicator is positionable along a side of the head of the patient and at a distance from an ear of the patient which includes a distance between the ear and an adjacent eye of the patient.

25. The apparatus of claim 24 wherein the indicator includes an elongated body.

26. The apparatus of claim 24 including an indicator mark for positioning on a face of the patient at a position of a lower portion of an eye socket of the patient.

27. The apparatus of claim 25 wherein the elongated body has a longitudinal axis alignable with an ear of the patient and in which the elongated body extends generally in a direction toward a top of the head of the patient.

28. The apparatus of claim 27 including an ear locator member alignable with the ear of the patient in association with the elongated body of the indicator in which a longitudinal axis of the elongated body of the indicator intersects the ear locator member.

29. The apparatus of claim 28 wherein the elongated body of the indicator and the ear locator member are carried by an ear locator bracket member.

30. The apparatus of claim 29 wherein the elongated body includes a slot which extends entirely through and which is defined by the ear locator bracket member.

31. The apparatus of claim 29 wherein the x-ray emitting source is mounted to an arm member rotatably mounted on a pivot member for rotating the arm member about an axis of rotation and wherein the ear locating bracket member is coupled to the arm member such that the ear locator member rotates with the arm member and in alignment with the axis of rotation and the elongated body of the visual indicator maintains a position transverse to the direction of the emission of the x-rays from the x-ray emitting source.

32. The apparatus of claim 31 wherein the arm member is elongated.

33. The apparatus of claim 31 wherein the x-ray emitting source is spaced apart from the axis of rotation.

34. The apparatus of claim 33 wherein the x-ray emitting source is positioned for emitting x-rays toward the axis of rotation.

35. The apparatus of claim 33 wherein the x-ray emitting source is positioned closer to an opposing end of the arm member than to the x-ray emitting source.

36. The apparatus of claim 35 wherein the axis of rotation is positioned closer to an opposing end of the arm member than to the x-ray emitting source.

37. The apparatus of claim 33 including an x-ray film holder fixedly secured to the arm member and is spaced apart from the axis of rotation on an opposite side of the axis of rotation from the x-ray emitting source.

38. The apparatus of claim 37 including a bracket apparatus fixedly secured to the x-ray film holder and fixedly secured to the arm member.

39. The apparatus of claim 37 wherein the x-ray film holder is aligned with the axis of rotation and the x-ray emitting source to receive x-rays from the x-ray emitting source.

40. The apparatus of claim 29 wherein the ear locating member is coupled to the arm member with the ear locator bracket member connected to a bracket apparatus which is fixedly mounted to the arm member.

41. The apparatus of claim 40 wherein the ear locating bracket member is rotatably mounted to the bracket apparatus permitting the at least one ear locator member to rotate about another axis of rotation transverse to the axis of rotation.

42. The apparatus of claim 41 wherein the other axis of rotation is perpendicular to the axis of rotation.

43. The apparatus of claim 42 wherein the axis of rotation and the other axis of rotation intersect.

44. A method for taking an x-ray of a patient's head, comprising the steps of:
providing an x-ray emitting source which is rotatable about an axis of rotation in which at least one ear locating member is aligned with and rotatable about the axis of rotation; and
positioning the patient's head to have an ear of the patient align with one of the at least one ear locator members.

45. The method of claim 44 wherein the step of providing includes the x-ray emitting source and the ear locator member rotate in conjunction with each other.

46. The method of claim 45 wherein the step of providing includes providing an arm member rotatably mounted to a pivot member for rotating the arm member about the axis of rotation, in which the arm member carries the x-ray emitting source at one position on the arm member and an x-ray film holder spaced apart from the x-ray emitting source along a length of the arm member, in which the axis of rotation is positioned between the x-ray emitting source and the x-ray film holder and in which at least one ear locator member is coupled to the arm member to rotate with the arm member and in alignment with the axis of rotation.

47. The method of claim 44 wherein the step of providing includes providing two ear locator members.

48. The method of claim 47 wherein the step of positioning includes aligning each ear of the patient with the two ear locator members.

49. The method of claim 48 wherein the step of positioning includes positioning the face of the patient in the direction of the x-ray emitting source.

50. The method of claim 48 including the step of positioning an x-ray film holder aligned with the patient's head and the x-ray emitting source and on an opposite side of the patient's head than the x-ray emitting source.

51. The method of claim 50 including the step of emitting x-rays from the x-ray emitting source providing a frontal x-ray image of the head of the patient.

52. The method of claim 47 wherein the step of positioning includes providing the ear locator members rotatably mounted to the arm member to rotate about another axis of rotation which is transverse and intersects the axis of rotation.

53. The method of claim 52 wherein the step of positioning includes positioning the ear locator members aligned in a direction in which the x-ray emitting source emits x-rays.

54. The method of claim 53 including the step of positioning an x-ray film holder aligned with the patient's head and the x-ray emitting source and on an opposite side of the patient's head than the x-ray emitting source.

55. The method of claim 54 including the step of emitting x-rays from the x-ray emitting source providing a side x-ray image of the head of the patient.

56. The method of claim 54 wherein the step of positioning includes positioning the ear locator members out of alignment with the direction of x-rays emitted from the x-ray emission source such that a line determined by the ear locator members forms an acute angle with the direction of x-rays emitted.

57. The method of claim 56 wherein the step of positioning the ear locators includes the line forming an angle of 45 degrees with the direction of x-rays emitted.

58. The method of claim 47 wherein the step of positioning includes positioning the face of the patient generally in the direction of the x-ray emitting source.

59. The method of claim 58 including the step of rotating the x-ray emitting source in a downward direction relative to the two ear locator members.

60. The method of claim 59 including the step of rotating the arm member in the range of 20 to 50 degrees from horizontal.

61. The method of claim 59 including the step of positioning an x-ray film holder aligned with the head of the patient and the x-ray emitting source and on an opposite side of the head of the patient than the x-ray emitting source.

62. The method of claim 59 including the step of rotating the patient's head from a generally vertical orientation backwards to a position such that a plane determined by an eye of the patient and ear is transverse to the direction of the x-rays emitted from the x-ray emitting source.

63. The method of claim 62 wherein the step of rotating includes positioning a Frankfort plane of the patient perpendicular to the direction of emission of x-rays.

64. A method for taking an x-ray of a head of a patient, comprising the steps of:
providing indicator coupled to an x-ray emitting source in which the indicator and x-ray emitting source rotate in conjunction and in the same direction with each other, and in which the indicator locates a plane alignable with an ear of the patient;
providing at least one ear locator positionable along an axis of rotation of the indicator;
aligning the ear of the patient with the indicator; and
positioning at least one eye of the patient in alignment with the plane.

65. The method of claim 64 wherein the step of providing includes the indicator and the x-ray emitting source having a common axis of rotation.

66. The method of claim 65 wherein the step of providing includes providing at least one ear locator aligned with the axis of rotation and rotatable about the axis of rotation in conjunction with the x-ray emitting source and the indicator.

67. The method of claim 66 wherein the step of providing includes providing one ear locator for each ear.

68. The method of claim 67 wherein the step of aligning includes positioning the one ear locator into alignment with each ear of the patient.

69. The method of claim 68 wherein the step of aligning includes positioning the patient to face generally in a direction of the x-ray emitting source with a plane of the face generally perpendicular to the ground and to the direction of the emission of x-rays.

70. The method of claim 69 including the step of rotating the x-ray emitting source in a downward direction relative to the axis of rotation.

71. The method of claim 70 including the step of providing an indicator mark on the face of the patient at a lower portion of an eye socket of the patient.

72. The method of claim 71 wherein the step of positioning includes rotating the head of the patent in a backward direction until the indicator mark aligns with the plane.

73. The method of claim 72 including the step of positioning an x-ray film holder aligned with the head of the patient and the x-ray emitting source and on an opposite side of the head of the patient than the x-ray emitting source.

74. The method of claim 73 including the step of emitting x-rays from the x-ray emitting source.

75. The method of claim 65 wherein the step of providing includes providing an arm member rotatably connected to a pivot member at the axis of rotation, in which the x-ray emitting source is mounted to the arm member and the indicator is connected to the arm member such that the plane is perpendicular to the direction of emission of x-rays.

76. The method of claim 65 including positioning the ear of the patient in alignment with the axis of rotation.

77. The method of claim 76 including the step of positioning the x-ray emitting source below a level of the ear of the patient.

78. The method of claim 77 wherein the step of providing includes the plane is transverse to the direction of an emission of x-rays.

79. The method of claim 78 including the step of emitting x-rays from the x-ray emitting source.

80. The method of claim 78 including the step of providing the plane perpendicular to the direction of the emission of x-rays.

81. The method of claim 78 including maintaining the plane perpendicular to the direction of the emission of x-rays.

82. The method of claim 64 wherein the step of providing includes positioning the indicator along a side of the head of the patient.

* * * * *

UNITED STATES PATENT AND TRADEMARK OFFICE
CERTIFICATE OF CORRECTION

PATENT NO. : 6,863,440 B2
DATED : March 8, 2005
INVENTOR(S) : Sildve et al.

It is certified that error appears in the above-identified patent and that said Letters Patent is hereby corrected as shown below:

Column 9,
Line 26, change "the" to -- a --.

Column 10,
Line 42, delete "aligned with and rotatable about" to -- positioned in --.

Column 11,
Line 55, after "providing" insert -- a --.

Column 12,
Line 28, change "patent" to -- patient --.

Signed and Sealed this

Twenty-seventh Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,863,440 B2
DATED : March 8, 2005
INVENTOR(S) : Sildve et al.

It is certified that error appears in the above-identified patent and that said Letters Patent is hereby corrected as shown below:

Column 12,
Lines 7-9, delete "step of providing includes providing at least one ear locator aligned with the axis of rotation and"; and before "rotatable" add -- ear locator is --.
Line 9, after "rotation" (second occurrence) insert -- and rotates --.

Signed and Sealed this

Twenty-ninth Day of November, 2005

JON W. DUDAS
*Director of the United States Patent and Trademark Office*